US008101888B2

(12) United States Patent
Kiessl et al.

(10) Patent No.: US 8,101,888 B2
(45) Date of Patent: Jan. 24, 2012

(54) DEVICE FOR THE INFRARED RADIATION OF SCALP HAIR

(75) Inventors: Stefan Kiessl, Bad Karlshafen (DE); Martin Liebeck, Darmstadt (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/183,472

(22) Filed: Jul. 31, 2008

(65) Prior Publication Data
US 2009/0062889 A1    Mar. 5, 2009

(30) Foreign Application Priority Data
Jul. 31, 2007    (EP) ..................................... 07113555

(51) Int. Cl.
*H05B 1/00*    (2006.01)
*A61N 5/06*    (2006.01)

(52) U.S. Cl. ........ 219/217; 219/228; 219/553; 219/222; 34/96; 34/97; 34/98; 34/99; 34/100; 34/101; 132/212; 607/88

(58) Field of Classification Search .................. 219/228, 219/217, 553, 222, 347–8; 34/96–101; 132/212; 607/88
See application file for complete search history.

(56) References Cited

U.S. PATENT DOCUMENTS

| 4,910,382 | A | 3/1990 | Kakuya et al. |
| 5,063,688 | A | 11/1991 | Moll et al. |
| 6,654,549 | B1 | 11/2003 | Konishi |
| 7,479,618 | B2 * | 1/2009 | Liebeck et al. ............... 219/217 |
| 2002/0048452 | A1 | 4/2002 | Shimizu |

OTHER PUBLICATIONS

European Search Report, dated Dec. 20, 2007, 4 pages.

* cited by examiner

*Primary Examiner* — Shawntina Fuqua
(74) *Attorney, Agent, or Firm* — Angela Marie Stone; Marianne Dressman

(57) ABSTRACT

A device (1.1) for the radiation of scalp hair (2) using infrared radiation (10.3), wherein the infrared radiation (10.3) is generated by at least one linear-shaped infrared lamp (3.1) with a reflector system (4). In a first exemplary embodiment, a first reflector (6.1) is allocated to the infrared lamp (3.1) on the longitudinal side, wherein the infrared lamp (3.1) basically forms an optical collection line of the first reflector (6.1). The first reflector (6.1) with a first reflection side (9.1) and a second reflector (6.2) with a second reflection side (9.2) are placed facing each other, wherein the infrared lamp (3.1) is enclosed by the first and the second reflector (6.1, 6.2), by at least 360° altogether.

6 Claims, 6 Drawing Sheets

DEVICE FOR THE INFRARED RADIATION OF SCALP HAIR

FIELD OF THE INVENTION

The invention relates to a device for the infrared radiation of scalp hair, wherein the infrared radiation is generated by at least one infrared lamp with a reflector system.

BACKGROUND OF THE INVENTION

These types of devices are known in the most varied of embodiments and are primarily used in hair salons to treat scalp hair that has been treated with an agent (for example permanent wave agent, styling agent, or colorant) using heat radiation (infrared radiation). EP0372443A1 discloses, for example, a device for the infrared radiation of scalp hair, which has a high level of infrared radiation dispersion through the reflector system because of the design, and which is also not very efficient in terms of energy. In addition, the device is relatively expensive to manufacture because of the design.

The object of the invention is to obtain a device for the infrared radiation of scalp hair that enables the even distribution of heat to the scalp hair, has improved efficiency with respect to energy and a design that is easily manufactured, and that enables a reduction in the manufacturing costs through simple measures.

SUMMARY OF THE INVENTION

This object is achieved by a first solution according to the characterizing features of independent Claim 1 and by a second solution according to the characterizing features of independent Claim 3.

Additional advantageous further embodiments of the invention according to the features of Claim 1 and/or 3 result from the sub-claims.

The invention results in the following advantages in particular:

1. Controlled radiation guidance, minimal radiation losses, high-level efficiency.
2. The external third reflector (of the first exemplary embodiment) is a "passive" component without its own infrared lamp, which means there are no heating problems, no protective screen, and no electrical components required for safety reasons.
3. Only one infrared lamp element is required, which results in easy and inexpensive electrical actuation.
4. Simple mechanical construction without moving parts, high-level mechanical stability, low inherent weight, economical manufacturing costs, and compact storage and packaging volumes due to the low design height.
5. The area with the thermal stress and electrical components for safety is spatially only limited to the second reflector (for the first exemplary embodiment).
6. Light, airy, and delicate appearance of the device, also available in a transparent design.
7. Users have an unobstructed view and head room, because the device is positioned over the head.
8. The third reflector or fifth reflector can optionally be constructed from transparent plastic with an optical transparent infrared lamp reflection layer (low-emission layer technology).

BRIEF DESCRIPTION OF THE DRAWINGS

The invention is explained in greater detail using two different exemplary embodiments. The following is shown.

DETAILED DESCRIPTION OF THE INVENTION

Figure 1:
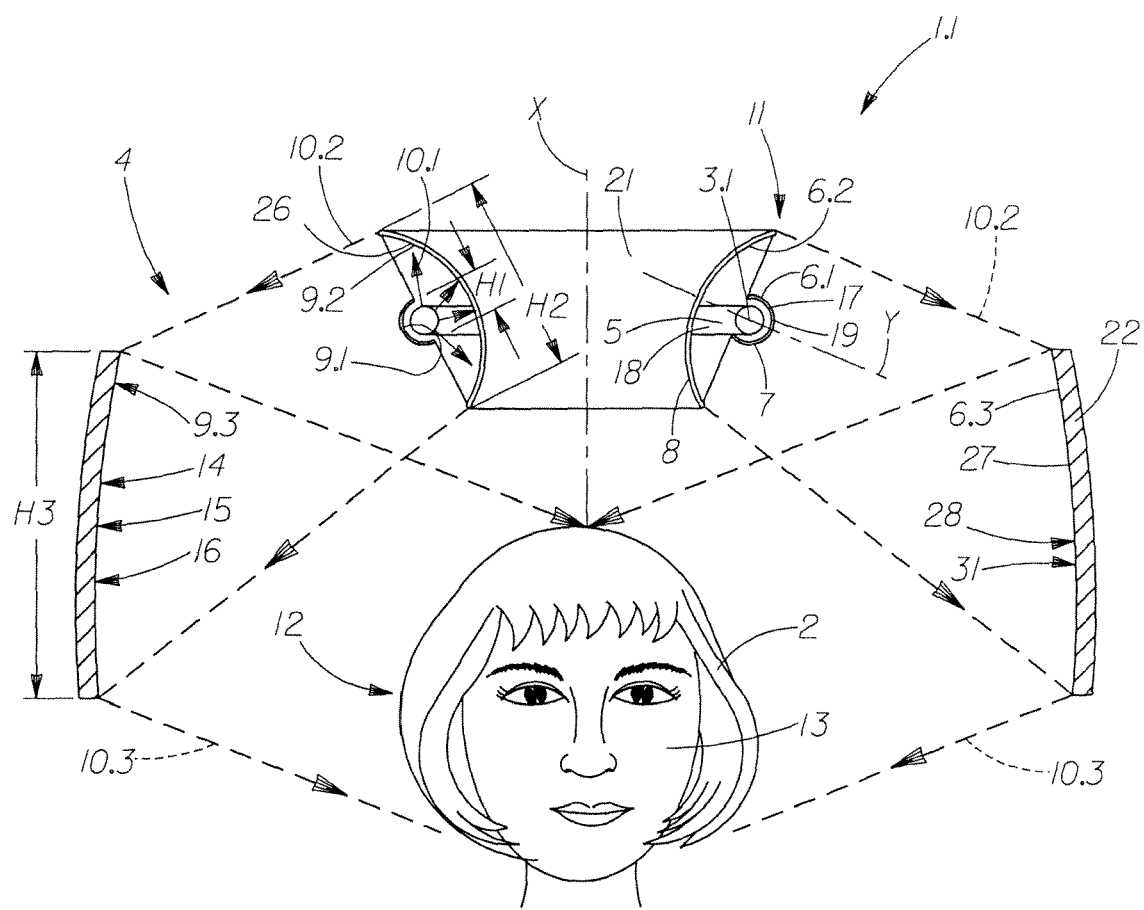
FIG. 1 shows a sectional representation of a first device of a first exemplary embodiment.

FIG. 1 shows a first device 1.1 for the radiation of scalp hair 2 using infrared radiation 10.3, wherein the infrared radiation 10.3 is generated by at least one first linear-shaped infrared lamp 3.1 with a reflector system 4.

A first reflector 6.1 is allocated to the infrared lamp 3.1 on the longitudinal side, wherein the infrared lamp 3.1 basically forms an optical collection line of the first reflector 6.1. The first reflector 6.1 with a first reflection side 9.1 and a second reflector 6.2 with a second reflection side 9.2 are placed facing each other, wherein the infrared lamp 3.1 is enclosed by the first and the second reflectors 6.1, 6.2, by at least 360°.

A third reflector 6.3 has a third reflection side 9.3, wherein a first infrared radiation output 10.1 of the first reflection side 9.1 impacts the second reflection side 9.2, a second infrared radiation output 10.2 of the second reflection side 9.2 impacts the third reflection side 9.3, and a third infrared radiation output 10.3 of the third reflection side 9.3 radiates the scalp hair 2.

The infrared lamp 3.1 basically forms a ring 5, which is held in place by the first reflector 6.1 with a bent first cross-section 7. The second reflector 6.2 is basically designed like a ring with a bent second cross-section 8. The first reflector 6.1 with the first reflection side 9.1 and the second reflector 6.2 with the second reflection side 9.2 are placed facing each other, wherein the infrared lamp 3 is enclosed by the first and the second reflectors 6.1, 6.2, by at least 360° (minimization of dispersed radiation). The third reflector 6.3, which is basically designed like a ring, is arranged with the third reflection side 9.3, wherein the second infrared radiation output 10.2 of the second reflection side 9.2 impacts the third reflection side 9.3. The third infrared radiation output 10.3 of the third reflection side 9.3 radiates the scalp hair 2, wherein the entire third infrared radiation output 10.3 is a reflection of the second infrared radiation output 10.2 through the third reflection side 9.3 (minimization of dispersed radiation).

The first reflector 6.1 in this case is designed as a thin gold layer 19, which is placed directly on the surface of the fused quartz tube 18 of the infrared lamp 3.1, preferably by vacuum metallizing. The gold layer 19 in this case covers a segment of the circular cross-section of the infrared lamp 3.

The first reflector 6.1 and the second reflector 6.2 together enclose the quartz lamp 3.1 in the cross-section, by at least 360° altogether. This prevents any infrared radiation that is coming directly from the fused quartz tube 18 from reaching the outside in an uncontrolled manner, whereby the efficiency level is significantly improved due to the prevention of dispersed radiation.

A significant advantage (visually as well as with respect to costs) can be seen in the fact that the first reflector 6.1 is applied directly to the fused quartz tube 18 as a gold layer 19, such that two functions are combined in one component. The first reflector 6.1, however, can also be designed as a separate component made of metal, which can then be positioned separately from the fused quartz tube 18. Depending on the geometric design, it is possible for this component to meet the corresponding safety standards for contact protection for the quartz lamp, whereby a separate covering screen is not required.

The entire third reflection side 9.3 of the third reflector 6.3 preferably has an optical free-form surface 16, on which the impacting infrared radiation 10.2 is precisely reflected for even infrared radiation 10.3 of the scalp hair surface 2. This free-form surface 16 cannot be defined by a mathematically closed shape but rather is the result of a complex graphic computer calculation.

Figure 2:
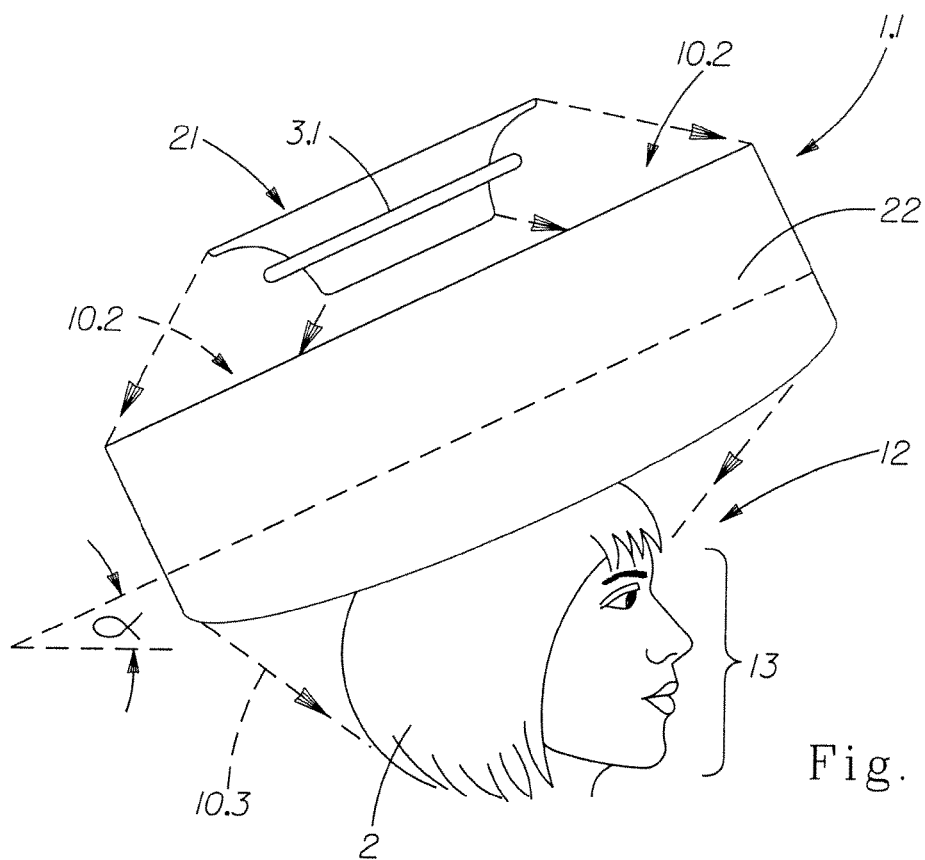
FIG. 2 shows a side view of the device according to FIG. 1.

FIG. 2 shows a side view of the first device 1.1 according to FIG. 1, which indicates the infrared radiation pattern of the second and third infrared radiation output 10.2, 10.3. The infrared radiation source 3.1 and the three reflectors 6.1, 6.2, 6.3 are shaped like a ring and arranged concentrically with respect one another.

Figure 3:
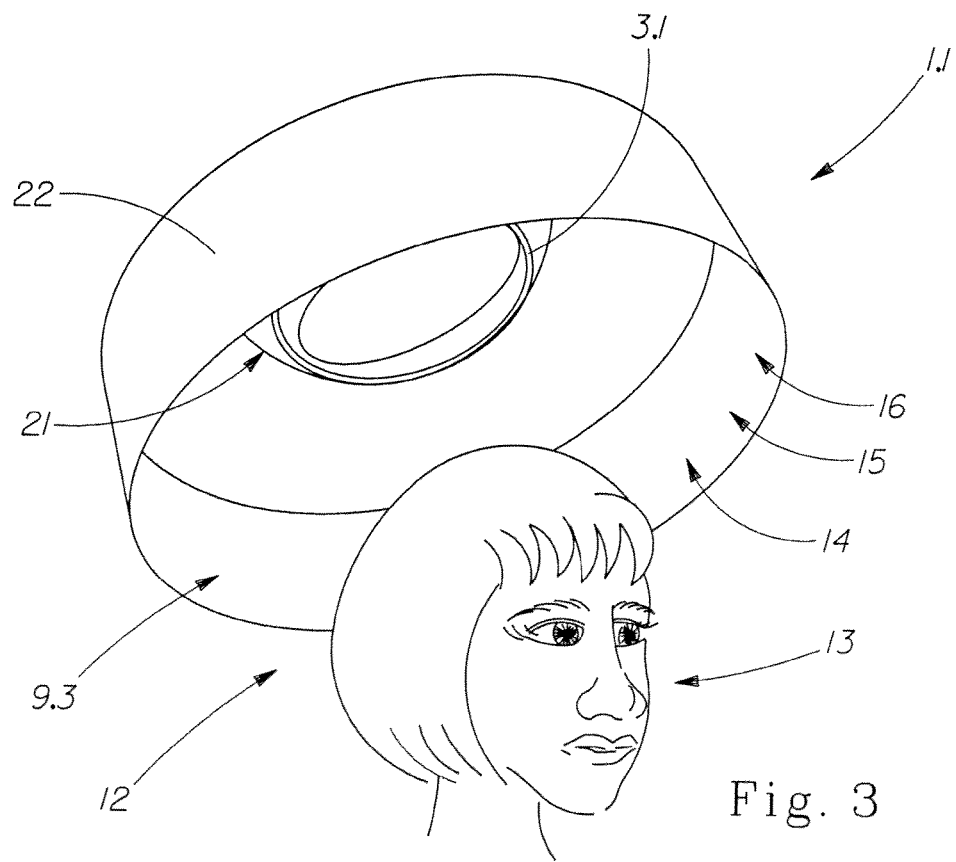
FIG. 3 shows a perspective side view of the device according to FIG. 1.

FIG. 3 shows a more detailed view of the first device 1.1 according to FIG. 1 in a perspective side view.

Figure 4:
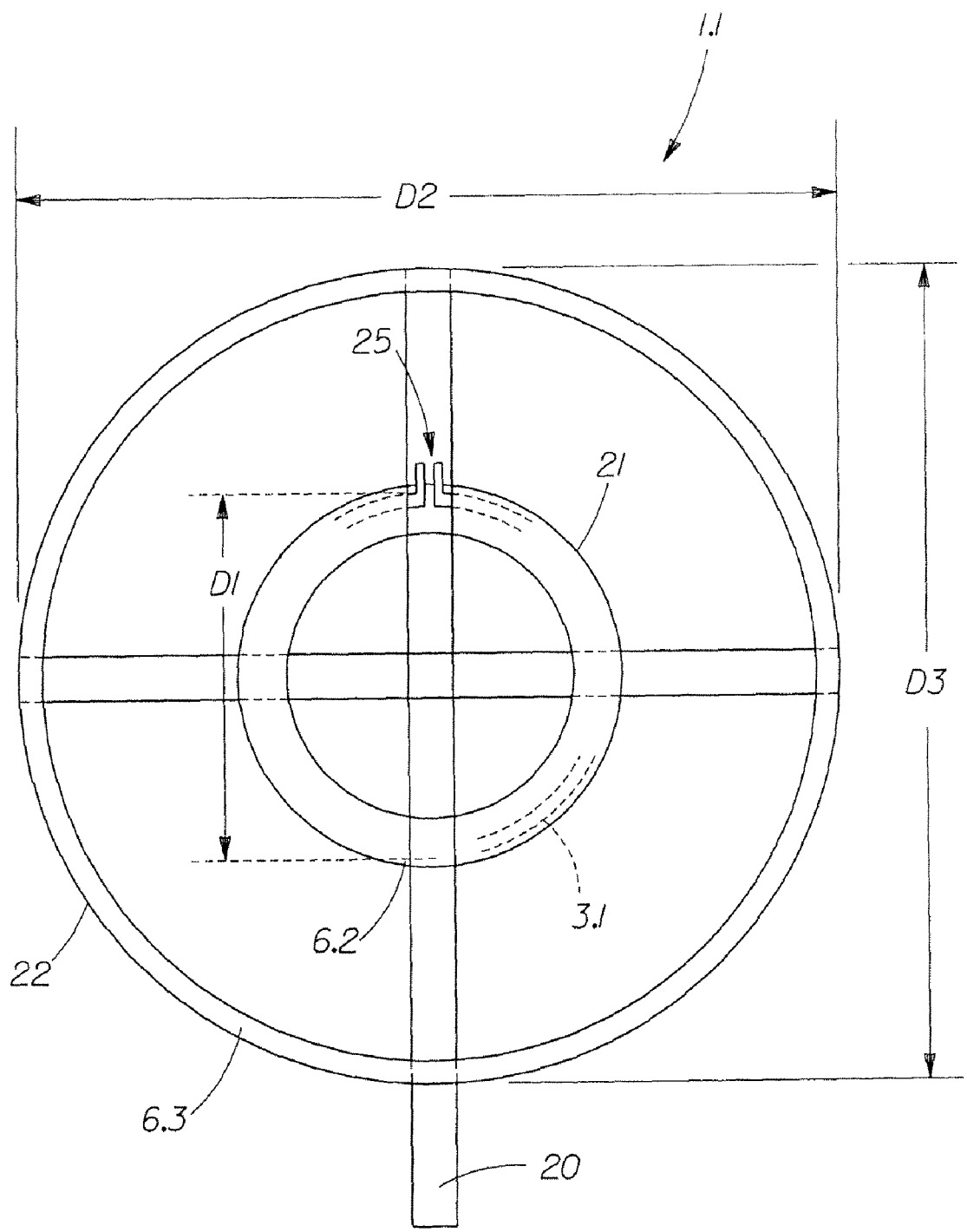
FIG. 4 shows a view of the device according to FIG. 1 from below.
Figure 5:
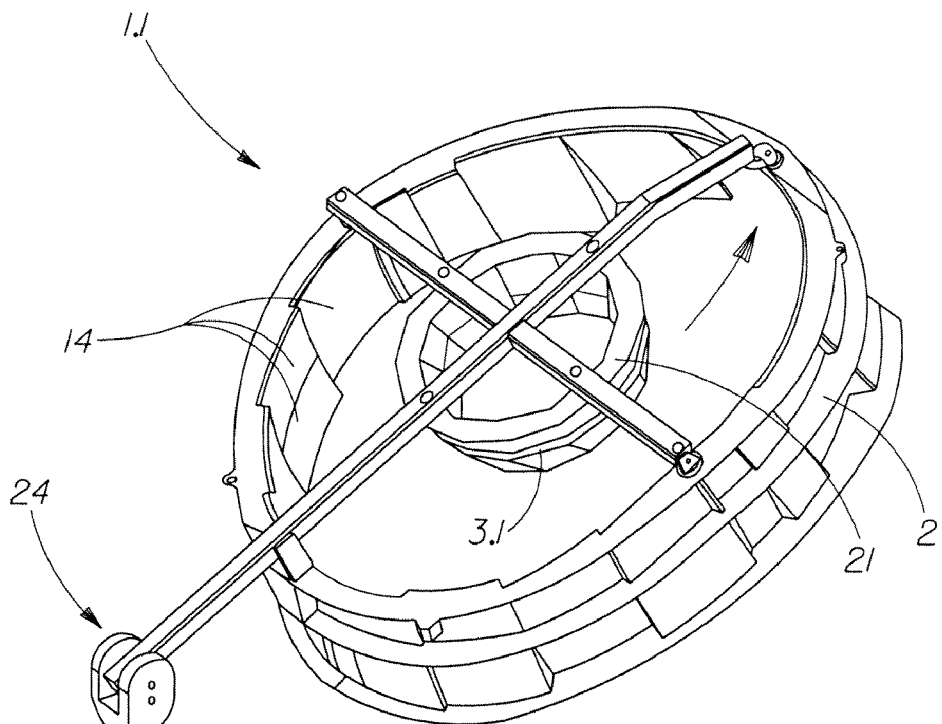
FIG. 5 shows a perspective side view of the device according to FIG. 1, but with reflector facets.
Figure 6:
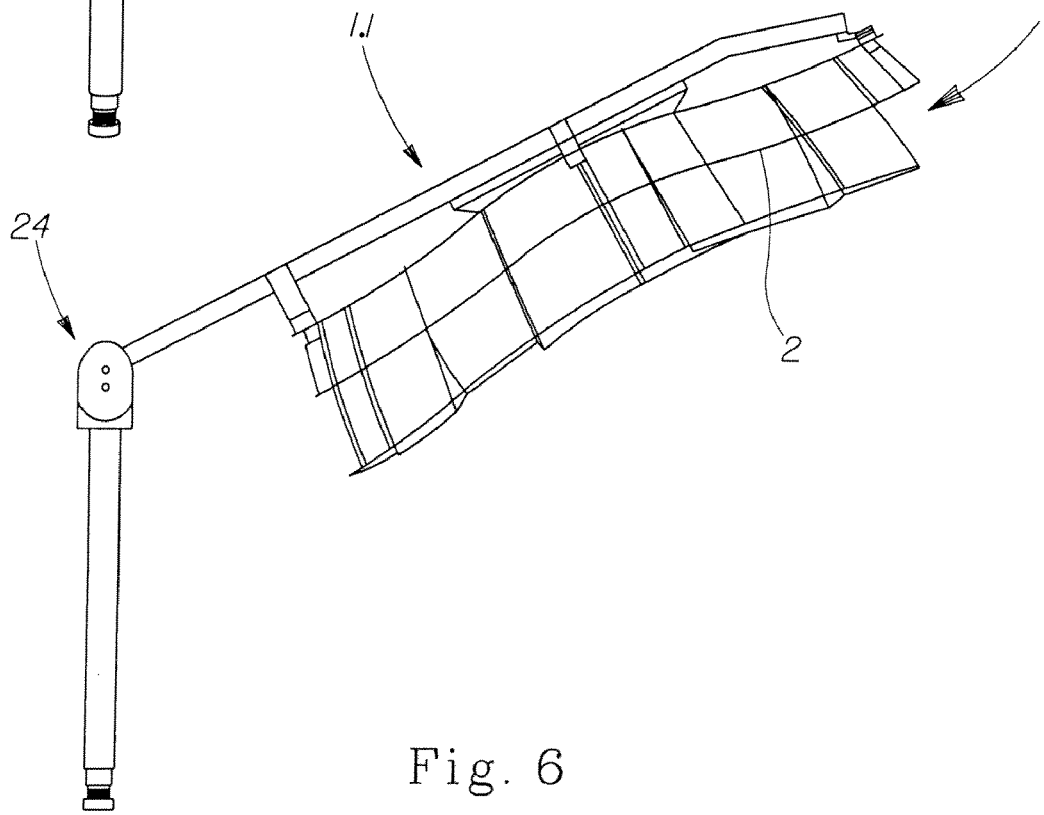
FIG. 6 shows a side view of the device according to FIG. 5.

FIG. 4 shows a view from below of the first device 1.1 according to FIG. 1, but with a retaining device 20 of the first and the second reflector mount 21, 22 as well as with a stand 24, wherein proven dimensions from use in the field are as follows:

The first infrared lamp 3.1 has a diameter D1 of approximately 200 mm and the third, circular reflector 6.3 has a diameter D3 of roughly 550 mm. With the oval-shaped design of the third reflector 6.3, diameter D3 is also approximately 550 mm, while diameter D2 is only approximately 500 mm. In addition to the precise radiation guidance through a multilayered reflection or through indirect radiation, the oval-shaped design of the third reflector 6.3 also results in more even radiation of the scalp hair 2, because this shape is roughly the shape of a human head, as it is when viewed from above.

The infrared lamp 3.1, which is enclosed by a first reflector 6.1, surrounds the inner, preferably circular-shaped, second reflector 6.2. The third reflector 6.3 forms external ring of the reflector system 4.

The three reflectors 6.1, 6.2, 6.3 and the infrared lamp 3.1 are always constructed to be a mirror image according to the alignment with respect to the scalp hair 2 of a person 12 (left/right sides of the head receive equal radiation).

For the electrical actuation of the infrared lamp 3.1 with a user interface including temperature selection, time preselection, etc., there are corresponding means provided that can be used within the scope of measures known in the field.

The first infrared lamp 3.1 in this case is a circular bent quartz tube 18 with an interior heating coil. Both ends are held together very tightly; that is where the electrical connections 25 exit.

The infrared radiation source 3.1 is a ring-shaped element that is circular in the cross-section. It should have the smallest diameter possible in order to correspond to the ideal for the optical point radiation source. A cross-sectional diameter of the infrared radiation source 3.1 of 6 mm has proven to be suitable in the field.

The heating capacity is normally constant along the perimeter, but there can be zones with different heating capacities according to the design of the entire system.

The second reflector 6.2 is a circular component that is symmetrical in its rotational axis in the cross-section. The cross-sectional surface 8 in this case is shaped as a parabola. In a view of the cross-section in this case, the fused quartz tube 18 lies on symmetrical axis Y of the parabola 26. The parabola opening points downwards diagonally and is facing the third reflector 6.3.

The second reflector 6.2 is preferably constructed from metal. The surface of the second reflector 6.2 has the highest level of infrared radiation reflection possible, preferably more than 90%, as well as a very low level of roughness, so that dispersed radiation is kept to a minimum. The cross-sectional surface 8 does not have to be shaped as a parabola. It is also possible, for example, to have a cross-sectional surface 8 with a center kink. This makes it possible to realize other optical properties of the exiting beam.

The third reflector 6.3 is a ring-shaped component similar to a cylinder jacket. The cross-sectional surface 27 is normally not constant along the perimeter, i.e. there are areas with differing cross-sectional surfaces 27 of the third reflection side 9.3. The reflector surface 28 of the third reflection side 9.3 comprises facets 14 or of edge-smoothed facets 15 or preferably of an optical free-form surface 16.

The third reflector 6.3 is a relatively large, complex component, which can be produced from plastic, which then must be provided with a mirror layer 28 on the surface. The surface of the reflector 6.3 should have the highest possible level of infrared radiation reflection (>90%) as well as a very low level of roughness, so that a minimal amount of dispersion occurs.

The third reflector 6.3 does not have to be a completely circular component; a subdivision into multiple separate elements or subsections (with minimal space in between) is also possible. A design height H3 (FIG. 1) of the third reflector 6.3 of approximately 120 mm has proven to be suitable in the field.

Position of head 12: The head 12 should be underneath the second reflector 6.2, enclosed by the third reflector 6.3 (FIG. 1).

The first device 1.1 has an adjustment angle, alpha, of approximately 27° (FIG. 2) with respect to the horizontal line that corresponds to the hairline.

According to the properties of the third reflector 6.3 and/or the direction of the radiation reflected by the third reflector 6.3, there is an optimal position for the head in which the desired radiation distribution is particularly well achieved.

Function of the reflector system 4: The second reflector 6.2 captures the infrared radiation being output from behind by the fused quartz tube 18 and reflects it toward the outside as a bundled, parallel beam (11° angle of divergence in this case). The angle of radiation and the angle of divergence as well as the radiation intensity are constant along the circular perimeter of the second reflector 6.2. The first reflector 6.1 covers the radiation area of the fused quartz tube 18 not captured by the second reflector 6.2 directed toward the front and reflects this part of the radiation back onto the second reflector 6.2 and into the fused quartz tube 18 as well. This ensures that no radiation unintentionally reaches the outside.

The second reflector 6.2 is designed so that the exiting radiation with the corresponding divergence angle illuminates the third reflector 6.3 completely, with the set distance, whereby this does not result in any significant excessive radiation beyond the edge of the third reflector 6.3.

The third reflector 6.3 then reflects the radiation coming from the second reflector 6.2 and impacting the head 12 and/or scalp hair 2 and ensures the desired spatial distribution of radiation onto the head 12 and/or the scalp hair 2. Areas without hair such as the field of vision and the ears are not radiated. The design/shape of the reflector surface 28 is of decisive importance for the radiation distribution.

Summary of the First Exemplary Embodiment:

The structural unit of the first and the second reflector 6.1, 6.2 has the function of deflecting, to the extent possible, the radiation emitted from the first infrared lamp 3.1, i.e. without any losses, as a directed, bundled beam and of guiding it to the third reflector 6.3. The third reflector 6.3 then reflects the radiation onto the head 12 and/or scalp hair 2 and ensures the desired radiation distribution and therefore the heat distribution at those locations. This involves indirect radiation, because the radiation 10.3 that is hitting the scalp hair 2 is not generated by the third reflector 6.3 itself (as is the case with the previous devices) but is only being redirected. The radiation source (infrared lamp 3.1) is spatially separated from this process.

Because the entire device 1.1 is shaped as a ring, it has the advantage in that dispersed radiation that results in the system 4 (on the fused quartz tube 18 itself as well as with each reflection) remains in the system 4 for the most part and is not reflected out from the sides, as would be the case, for example, with a linear system that has two open ends. The circular system 4 thus increases efficiency and has significantly less power consumption (400 W instead of 1000 W) and therefore a significantly improved level of efficiency as a result, with a comparable amount of radiation onto the scalp hair 2.

The third reflector 6.3 can optionally be constructed from transparent plastic 30 with an optical transparent infrared radiation reflection layer 17 (low emission layer technology), whereby the entire appearance of the device 1.1 is airier and visually less obtrusive.

Figure 7:
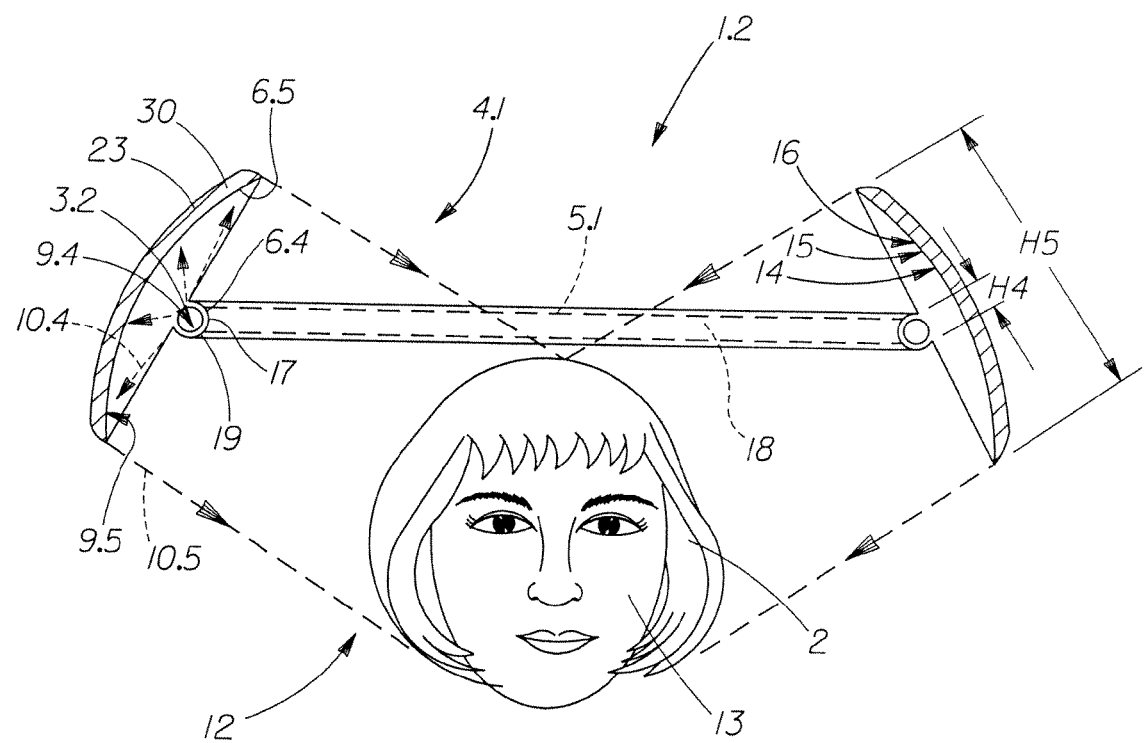
FIG. 7 shows a sectional representation of a second device of a second exemplary embodiment.

FIG. 7 shows a second device 1.2 of a second exemplary embodiment for the radiation of scalp hair 2 using infrared radiation 10.5, wherein the infrared radiation 10.5 is generated by at least one first linear-shaped infrared lamp 3.2 with a reflector system 4.1, with which precise radiation guidance is achieved due to two-layered reflection and a ring-shaped geometric arrangement. The device 1.2 is characterized in that a fourth reflector 6.4 is allocated to the infrared lamp 3.2 on the longitudinal side, wherein the infrared lamp 3.2 basically forms an optical collection line of the fourth reflector 6.4, that the fourth reflector 6.4 with a fourth reflection side 9.4 and a fifth reflector 6.5 with a fifth reflection side 9.5 are arranged facing one another, wherein the infrared lamp 3.2 is enclosed by the fourth and the fifth reflector 6.4, 6.5, by at least 360° altogether (minimization or prevention of dispersed radiation), wherein a fourth infrared radiation output 10.4 of the fourth reflection side 9.4 impacts the fifth reflection side 9.5, and a fifth infrared radiation outlet 10.5 of the fifth reflection side 9.5 radiates the scalp hair 2.

Optionally, the fourth and fifth reflector 6.4, 6.5 can be provided with the corresponding infrared lamp 3.2 in a suitable geometric arrangement as sections or sub-areas for radiating the scalp hair 2.

The infrared lamp 3.2 basically forms a ring 5.1, wherein the infrared lamp 3.2 is held in place by the fourth reflector 6.4. The fifth reflector 6.5 is basically designed like a ring. The fourth reflector 6.4 with a fourth reflection side 9.4 and the fifth reflector 6.5 with a fifth reflection side 9.5 are arranged facing one another, wherein the infrared lamp 3.2 is enclosed by the fourth and the fifth reflector 6.4, 6.5, by at least 360° altogether, and wherein the fifth infrared radiation output 10.5 of the fifth reflection side 9.5 radiates the scalp hair 2.

Figure 8:
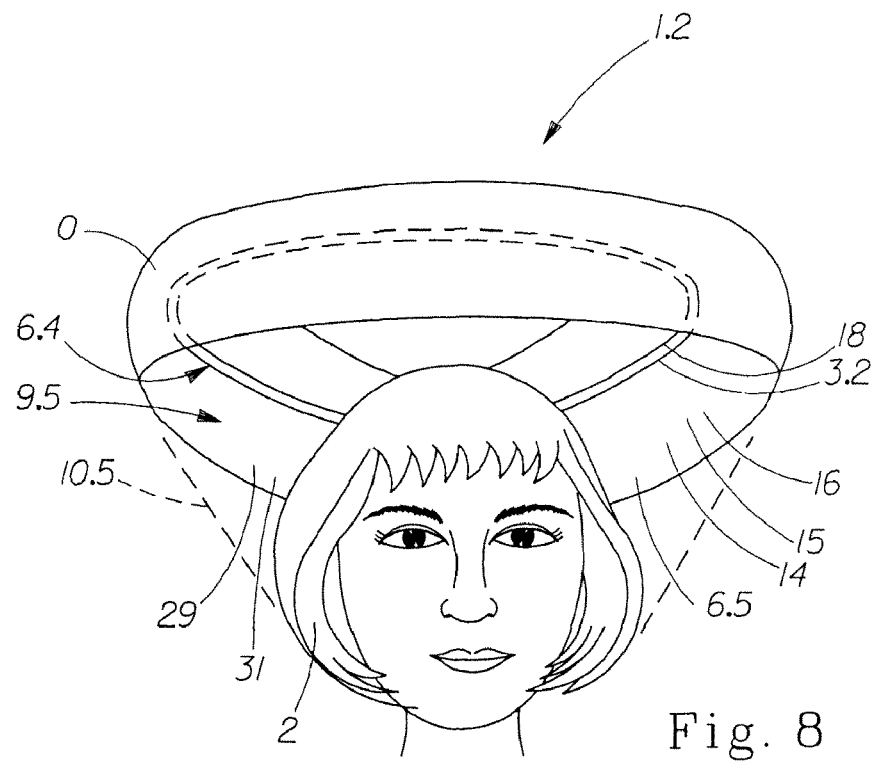
FIG. 8 shows a front view of the second device according to FIG. 7.

FIG. 8 shows a front view of the second device 1.2 according to FIG. 7. It comprises a second infrared lamp 3.2 and a fourth and a fifth reflector 6.4, 6.5. These components are shaped like a ring and arranged concentrically with respect to one another.

This second device 1.2 is similar to the first device 1.1, except that there is no second reflector 6.2, wherein, instead of this, the second infrared lamp 3.2 is allocated to the external, fifth reflector 6.5. In this case as well, direct infrared radiation is prevented by a fourth reflector 6.4. A significant difference in this case is in the significantly larger diameter of the second infrared lamp 3.2, which is almost as large as the external diameter D4 of the third reflector mount 23. The third and fifth reflectors 6.4, 6.5 and the second infrared lamp 3.2 are always constructed to be a mirror image according to their alignment with respect to the scalp 12, wherein the left and the right sides of the head receive equal radiation.

Figure 9:
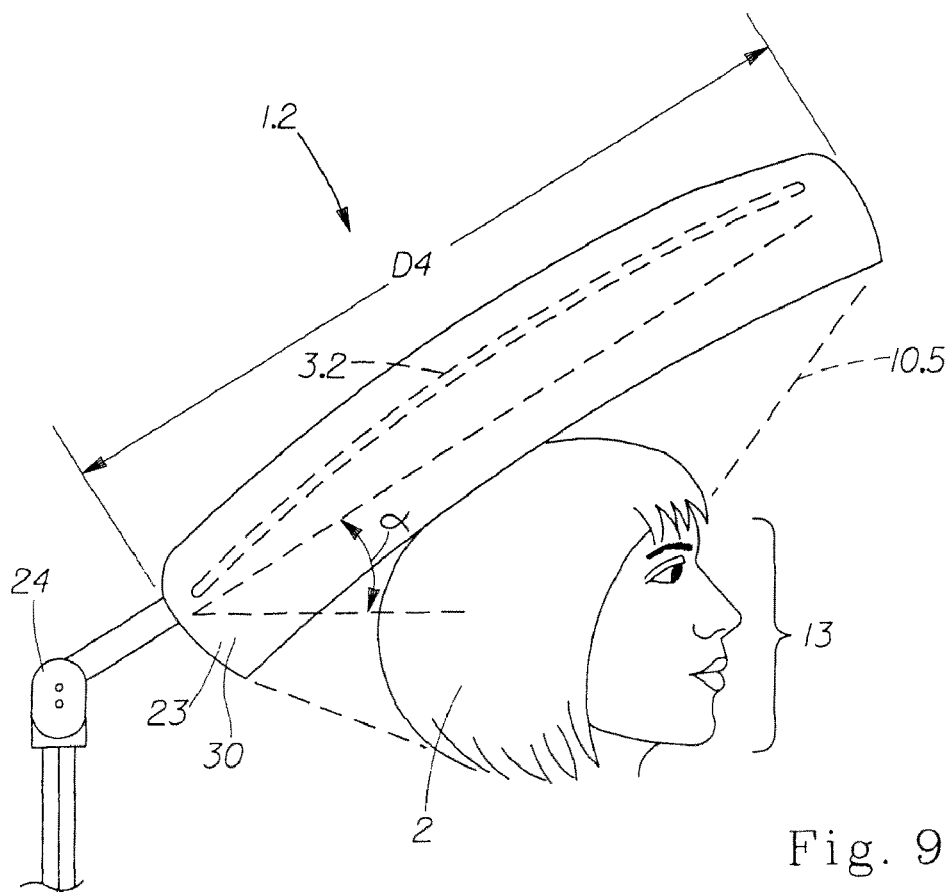
FIG. 9 shows a side view of the second device according to FIG. 8.

FIG. 9 shows a side view of the second device 1.2 according to FIG. 8. Constrained by the optical system 4, the second infrared lamp 3.2 has practically the same large diameter as the fifth reflector 6.5.

The following are provided as additional components:
A mechanical connection of the device 1.2 to a stand 24 (FIG. 9).
Retaining devices on the fifth reflector 6.5, which hold the second infrared lamp 3.2 in its position with respect to the fifth reflector 6.5.
An electrical actuation for the second infrared lamp 3.2 with a user interface with temperature selection, time preselection, etc.
An optional device, which facilitates and/or enables the correct positioning of the device 1.2 over the head 12 using mechanical or optical means.

The fifth reflector 6.5 is a ring-shaped component shaped like a gutter. The cross-sectional surface is normally not constant along the perimeter, i.e. there are areas with differing cross-sectional surfaces (free-form surface reflector).

The surface of the fifth reflector 6.5 should have the highest possible level of infrared radiation reflection (>90%) as well as a very low level of roughness, so that a minimal amount of dispersion is output.

The fifth reflector 6.5 does not have to be a completely circular component; a subdivision into multiple separate elements is possible. The external diameter D4 is approximately 550 mm.

Head position: The head 12 should be approximately central, underneath the fifth reflector 6.5. The second device 1.2 has an adjustment angle, alpha, of approximately 27° (FIG. 9) with respect to the horizontal line that corresponds to the hairline.

Due to the properties indicated of the fifth reflector 6.5 and/or the direction of the radiation reflected by the fifth reflector 6.5, there is an optimal position for the head in which the desired radiation distribution is particularly well achieved.

Functional Method:

The fifth reflector 6.5 captures the radiation being emitted by the fused quartz tube 18 toward the back and reflects it precisely onto the head. The fourth reflector 6.4 covers the radiation area of the fused quartz tube 18 not captured by the fifth reflector 6.5 directed toward the front and reflects this part of the radiation back onto the fifth reflector 6.5 and/or into the fused quartz tube 18 as well. This ensures that no radiation unintentionally reaches the outside (minimization of dispersed radiation and/or increase in efficiency).

The desired even distribution of radiation onto the scalp hair 2 is made possible by the corresponding design of the reflector surface 29.

Because the second device 1.2 is shaped as a ring, it has the advantage in that dispersed radiation that results in the system 4 (on the fused quartz tube 18 itself as well as with each reflection) remains in the system 4 for the most part and is not immediately reflected out from the sides, as would be the case, for example, with a linear system that has two open ends. The circular system 4 increases efficiency.

The reflector surface 29 of the fifth reflection side 9.5 comprises facets 14 or of edge-smoothed facets 15 or preferably of an optical free-form surface 16.

The third ring-shaped reflector mount 23 and/or the fifth ring-shaped reflector 6.5 results in a high level of mechanical stability.

The third reflector 6.3 and/or the fifth reflector 6.5 of the first and/or second device 1.1, 1.2 can consist of subsections with optional distances.

Optionally, the first or second linear-shaped infrared lamp 3.1, 3.2 comprises multiple straight-lined infrared lamps 3.1, 3.2, which are put together in a row, whereby the commercially available designs can be used.

A very unobtrusive appearance of the first and/or second device 1.1, 1.2 is characterized in that the second reflector mount 22 and the third reflector 6.3 (first device 1.1) and/or the third reflector mount 23 (first device 1.1) and the fifth reflector 6.5 (second device 1.2) consist of transparent material 30, preferably of plastic, and have a visually transparent infrared radiation reflection layer and/or mirror layer 31 in low-emission layer technology, whereby the entire appearance of the device 1.1, 1.2 is airier and less visually obtrusive.

A maximally even distribution of radiation onto the scalp hair 2 is supported in that the second and/or the third reflector mount 22, 23 has an adjustment angle, alpha, of roughly 27° with respect to the horizontal lines.

The entire fifth reflection side 9.5 of the fifth reflector 6.5 preferably has an optical free-form surface 16, on which the impacting infrared radiation 10.4 is precisely reflected for even infrared radiation 10.5 of the scalp hair surface 2. This free-form surface 16 cannot be defined by a mathematically closed shape but rather is the result of a complex graphic computer calculation.

PARTS REFERENCE LIST 1.1 First device
1.2 Second device
2 Scalp hair
3.1 First infrared lamp
3.2 Second infrared lamp
4 Reflector system
5 Ring
5.1 Ring
6.1 First reflector
6.2 Second reflector
6.3 Third reflector
6.4 Fourth reflector
6.5 Fifth reflector
7 Bent first cross-section
8 Bent second cross-section
9.1 First reflection side
9.2 Second reflection side
9.3 Third reflection side
9.4 Fourth reflection side
9.5 Fifth reflection side
10.1 First infrared radiation output
10.2 Second infrared radiation output
10.3 Third infrared radiation output
10.4 Fourth infrared radiation output
10.5 Fifth infrared radiation output
11 Hyperboloid/parabola symmetrical in its rotational axis
12 Head
13 Field of vision
14 Facets
15 Edge-smoothed facets
16 Optical free-form surface
17 Reflection layer
18 Fused quartz tube
19 Gold layer
20 Retainer device
21 First reflector mount
22 Second reflector mount
23 Third reflector mount
24 Stand
25 Connection
26 Parabola
27 Cross-sectional surface
28 Reflector surface (mirror layer)
29 Reflector surface (mirror layer)
30 Transparent material
31 Transparent mirror layer
Alpha adjustment angle
D1 First diameter
D2 Second diameter
D3 Third diameter
D4 Fourth diameter
H1 First height
H2 Second height
H3 Third height
X Axis
Y Axis The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A device for the radiation of scalp hair using indirect infrared radiation, wherein the indirect infrared radiation is generated by one linear-shaped infrared lamp with a reflector system, characterized in that
a first reflector (6.1) is allocated to the infrared lamp (3.1) on a longitudinal side, wherein the infrared lamp (3.1) basically forms an optical collection line of the first reflector (6.1);

the first reflector (6.1) with a first reflection side (9.1) and a second reflector (6.2) with a second reflection side (9.2) are arranged facing one another;

the infrared lamp (3.1) is enclosed by the first and the second reflector (6.1, 6.2), by at least 360° altogether;

a third reflector (6.3) is arranged with a third reflection side (9.3);

a first infrared radiation output (10.1) of the first reflection side (9.1) impacts the second reflection side (9.2); and a second infrared radiation output (10.2) of the second reflection side (9.2) impacts the third reflection side (9.3)); wherein the second reflector (6.2) does not generate the second infrared radiation output (10.2); and a third infrared radiation output (10.3) of the third reflection side (9.3) radiates to the scalp hair (2); wherein the third third reflector (6.3) does not generate the third infrared radiation output (10.3)

wherein the device has a power consumer of 400 W.

2. The device according to claim 1, wherein the first infrared lamp (3.1) basically forms a ring (5) and is held in place by the first reflector, and the second reflector (6.2) is basically designed like a ring.

3. A device for the radiation of scalp hair using indirect infrared radiation, wherein the indirect infrared radiation is generated by at least one linear-shaped infrared lamp with a reflector system, wherein a fourth reflector (6.4) is allocated to the infrared lamp (3.2) on a longitudinal side, wherein the infrared lamp (3.2) basically forms an optical collection line of the fourth reflector (6.4);

the fourth reflector (6.4) with a fourth reflection side (9.4) and a fifth reflector (6.5) with a fifth reflection side (9.5) are arranged facing one another;

the infrared lamp (3.2) is enclosed by the fourth and the fifth reflector (6.4, 6.5), by at least 360° altogether;

a fourth infrared radiation output (10.4) of the fourth reflection side (9.4) impacts the fifth reflection side (9.5); and a fifth infrared radiation output (10.5) of the fifth reflection side (9.5) radiates to the scalp hair (2); wherein the fifth reflector (6.4) does not generate the fifth infrared radiation output (10.5)

wherein the device has a power consumer of 400 W.

4. The device according to claim 1 wherein the infrared lamp (3.2) and the fourth reflector (6.4) basically form a ring (5.1).

5. The device according to claim 1, wherein the linear-shaped infrared lamp (3.1, 3.2) comprises multiple straight-lined infrared lamps (3.1, 3.2) in a row.

6. The device according to claim 3, wherein, optionally, the fourth and fifth reflector 6.4, 6.5 can be provided with the corresponding infrared lamp 3.2 in a suitable geometric arrangement as sections or sub-areas for radiating the scalp hair (2).

\* \* \* \* \*